United States Patent
Forgang et al.

(12) 
(10) Patent No.: US 6,603,309 B2
(45) Date of Patent: Aug. 5, 2003

(54) ACTIVE SIGNAL CONDITIONING CIRCUITRY FOR WELL LOGGING AND MONITORING WHILE DRILLING NUCLEAR MAGNETIC RESONANCE SPECTROMETERS

(75) Inventors: Stanislav W. Forgang, Houston, TX (US); Zinovy B. Krugliak, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/862,793

(22) Filed: May 21, 2001

(65) Prior Publication Data

US 2002/0171421 A1 Nov. 21, 2002

(51) Int. Cl.[7] .................................................. G01V 3/00
(52) U.S. Cl. ........................................ 324/303; 324/322
(58) Field of Search ................................ 324/303, 306, 324/307, 312, 314, 318, 322

(56) References Cited

U.S. PATENT DOCUMENTS

| | | | | |
|---|---|---|---|---|
| 4,701,711 A | * | 10/1987 | Willard et al. | 324/303 |
| 5,432,446 A |   | 7/1995 | MacInnis et al. | 324/303 |
| 5,828,216 A | * | 10/1998 | Tschudin et al. | 324/300 |
| 6,150,817 A | * | 11/2000 | Lurie et al. | 324/309 |

* cited by examiner

*Primary Examiner*—Louis Arana
(74) *Attorney, Agent, or Firm*—Madan, Mossman & Sriram, P.C.

(57) ABSTRACT

NMR transmitter/receiver antenna active signal conditioning circuitry that enables receiver antenna circuit protection from high voltage RF transmitter pulses, provides energy dumping for the entire antenna in successive stages and eliminates re-tuning during sweeping of the antenna frequency.

10 Claims, 4 Drawing Sheets

ACTIVE SIGNAL CONDITIONING CIRCUITRY FOR WELL LOGGING AND MONITORING WHILE DRILLING NUCLEAR MAGNETIC RESONANCE SPECTROMETERS

FIELD OF THE INVENTION

The present invention is related to the field of nuclear magnetic resonance ("NMR") sensing tools deployed in down hole well logging and monitoring while drilling environments. More specifically, the invention is related to a NMR well logging and monitoring while drilling tool that comprises an active antenna signal conditioning circuitry for providing multi-frequency measurements and respective suppression of noise.

DESCRIPTION OF THE RELATED ART

NMR well logging instruments are utilized for determining properties of earth formations including: the fractional volume of pore space, the fractional volume of mobile fluid filling the pore space and other petrophysical parameters. An NMR well logging instrument typically contains a permanent magnet to produce a static magnetic field in adjacent earth formations. The NMR well logging instrument typically includes a transmitting antenna assembly positioned near the magnet. The transmitting antenna assembly is shaped so that a pulse of radio frequency (RF) power irradiated by the antenna assembly induces a RF magnetic field in the adjacent earth formation. In the investigated volume of the surrounding borehole formation the induced RF magnetic field is generally orthogonal to the static magnetic field, thereby creating appropriate conditions for formation NMR excitation.

Following the RF antenna pulse, voltages representative of NMR precess in the formation are induced in the receiving antenna. In particular, these voltages represent precession rotation of hydrogen or some other nuclei spin axis about the static magnetic field produced by the NMR well logging tool. NMR tool designs typically use the same antenna for transmitting and receiving along with electronic modules for protecting a receiver small signal circuitry from potentially damaging high voltage conditions while transmitting.

There are various known NMR well logging instruments proposed and/or implemented for measuring NMR properties of substances, in particular, the properties of earth formations. One type of NMR instrument is described in U.S. Pat. No. 4,710,713 by Taicher et al. Another type of NMR instrument is described in U.S. Pat. No. 4,350,955 by Jackson et al. Both of these NMR instruments represent early designs of well logging NMR instruments with the main focus on the magnet assembly.

As commonly applied in NMR tools, a primary burst-type pulse of alternating magnetic field with radio frequency (–"the RF pulse") is irradiated by a transmitter antenna to be applied to a test sample, or in the case of a logging down hole apparatus, to be applied to the formation adjacent the well bore. The test sample or formation response—a magnetic field due to NMR nuclei spin axis precession—is typically measured and sampled at a later time, i.e., after the primary RF field has been removed. Typically, the primary transmitter RF pulse and the formation response occur at the same frequency. In this case there is no need for compensation in hardware or in post-processing to correct errors introduced by the primary field that might couple into the receiving antenna.

An "electronic" dynamic range of typical NMR operations, that is, the ratio of the primary RF excitation pulse voltage applied to the transmitter antenna to the secondary response voltage induced in the receiver antenna can be of the order of 240 dB or more. The combination of these two factors—same transmit and receive signal frequencies and such an enormous disparity between the excitation and response voltages creates well known receiver circuitry protection and signal-to-noise ratio design problems. Those who are skilled in the art would recognize that just mentioned problems could appear in both combined (single) and individual transmitter/receiver antenna NMR instrument configurations.

A single or combined transmitter/receiver antenna is generally utilized to provide better stability of the antenna transfer function with respect to excitation and response voltages and, in some applications, for design simplification. Typically, an antenna is provided as a tuned parallel resonant inductance/capacitance (LC) tank circuit with a high electrical quality value (Q), where the inductor L is magnetically coupled to an adjoining sample or formation that is being excited.

The RF pulse induced by the current flowing through the inductor L in the transmit mode excites the nuclei in the adjoining sample or formation. Driving the LC tank by the electronic module acting as a voltage source allows this inductor current magnitude to be almost independent from the tank tuning conditions. However, ability to tune a high electrical quality Q tank exactly to its resonance frequency enables a transmitter design with significantly less power consumption compared to a non-tuned antenna approach. This occurs due to a known fact that the output current drained from the driving electronics will be in Q times less than a resonance tank current itself.

In accordance with the principal of reciprocity, in the receive mode the magnetic field generated by the excited nuclei induces an electrical voltage across the inductor, L of the LC tank and thereby energizing it. This voltage becomes effectively amplified Q times if measured across the entire tank, i.e., across tank capacitor C. Useful additional features of a high Q resonant tank is the narrow filtering capability resulting both in filtering the induced signal and suppressing intrinsic Johnson noise outside of the antenna's pass-band. A combined transmitter/receiver antenna circuit, however, exhibits the most severe "electronic" dynamic range design problems. For example, in the NTMR arrangement, a transmitter driver voltage output pulse is applied in the range of 1,000 volts peak to the combined antenna, however, the response voltage induced by the formation in the combined antenna is only a few tenths of a nanovolt. If such a transmitter voltage is directly applied to the small signal receiver circuitry without an adequate protection, the circuitry would be saturated during the transmission pulse and then might require an inordinately long "dead" time for recovering after the primary RF pulse has been removed. Furthermore, if not properly protected, this relatively large transmission voltage could irreversibly damage the receiver circuitry. In order to avoid the potential damage a protection element or attenuator is placed between the antenna and the receiver circuitry's amplifier.

The attenuator has been designed to produce a high band pass signal attenuation during the RF field transmission, however, it might undesirably shrink the relatively miniscule response voltages in the receive mode, as well. Moreover, if the attenuator is somewhat noisy, its parasitic signals could be coupled back into the resonant tank circuit and their energy maybe enough to induce undesirable tank selfoscillations. These oscillations, being within the same frequency range as the input signal, would interfere with the acquired response from the formation apparently reducing the signal-to-noise ratio (SNR). To avoid developing excessive noise in the receive mode, a typical attenuator design would assume its disabling or bypassing during reception.

After RF pulse transmission is completed the energy that has been stored in the tank circuitry shall be quickly removed. Conventionally, this has been done by dumping an electronic module by active loading (or shunting) the resonant tank. That is, the electromagnetic energy stored in the tank after transmission is typically converted into the heat and dissipated. For those who are skilled in the art it should be seen that the quickest energy dissipation from the resonant tank happens when this module has been actively loaded with a resistor equal to the tank's critical impedance.

To further protect the receiver circuitry, the attenuator remains enabled until the dumped tank voltage drops down below a safe level specified by manufacturers of the components from which this circuit is built.

In order to deal with noise coming from other low voltage control circuits, typical NMR antenna circuit designs provide a separate receiver dump circuit that can also suppress the tank resonant qualities. The receiver dump is enabled after completing the energy removal from the tank below safe level, but before switching off the attenuator. It is disabled right before arrival of a respective formation response to the antenna.

Alternatively, separate transmitter and receiver antennas have been used to alleviate the dynamic range severity. The separate transmitter and receiver circuitry solves the problem only partially because the RF transmission pulse is applied directly to the transmitter antenna and is not applied directly to the receiver circuitry. In reality, a practical assembly will always contain some undesirable electromagnetic coupling between these two antennas: it could be capacitive or magnetic or, which happens more often, of both kinds. As the result of this unavoidable coupling the induced voltage in the receiver antenna associated with the transmission pulse can still be sufficiently large to saturate or even damage electronic components in the receiver circuitry. Thus, even in case of separate transmitter and receiver antennas there is also a need for hardware to protect the receiver electronics while the tool is in a transmit mode.

Operating conditions and requirements are different for down hole logging and monitoring applications, as opposed to laboratory conditions. Moreover, there is a significant difference between the capabilities of common laboratory NMR spectrometers and downhole NMR spectrometers. Laboratory NMR spectrometers generally utilize a primary magnetic burst of a single RF frequency for an entire set of tests. The laboratory measurements are generally more stable because of stable laboratory temperature and pressure environment. Thus, the tool electronic attenuators can be set and tuned to a single frequency. If a frequency change becomes necessary, for instance, due to an unsatisfactory test sample response, the laboratory NMR antenna and attenuator can be easily re-tuned to another frequency and the NMR measurement repeated. Laboratory NMR spectrometers usually utilize significantly higher operating frequencies than down hole NMR spectrometers that in some cases this may help to simplify laboratory re-tuning methods and hardware.

In well logging and monitoring while drilling NMR applications, however, NMR spectrometers necessarily operate with multiple and lower frequencies and must be functional within a wide range of temperatures that immediately results in less stable antenna and attenuator electrical parameters. Practically, this can be resolved if the attenuator has been designed as frequency independent, i.e., as required no re-tuning.

Typically, in the transmit mode the antenna has been driven by the above mentioned voltage source electronics with an output frequency controlled by crystal oscillators. By periodical compensation of the tank electrical losses a driver maintains a hard synchronization of the antenna current with its voltage (or a tool clock) and establishes a predefined RF pulse magnitude. This apparently simplifies requirements to the antenna stability in the transmit mode.

There are two difficulties encountered in employing a hard synchronization for an imperfectly tuned tank. The first one is associated with elevated tool power consumption, that is, the further apart the driver's synch and tank's resonance frequencies, the lower actual tank's electrical quality, its effective impedance and higher the driver output current.

The second problem appears in the receiver mode where the formation response has a frequency exactly equal to the driver's frequency response. Thus, if the antenna tuning in the receiver mode does not exactly match the synch, the induced voltage will be amplified less than in Q times. This voltage also will experience the LC tank's amplitude and phase frequency distortions, which lower the overall SNR. Typically, in well logging and measurement while drilling applications this signal deterioration doesn't significantly affect the receiver noise figure. Practically, it could be recovered by increasing the NMR train stacking level and possibly with some decreasing of the tool logging speed.

As it has been mentioned above, the most severe problem in NMR well logging apparatus appears when the attenuator has been designed as tunable. Thus, due to the abovementioned temperature influences it becomes difficult to keep attenuator tuning exactly matched to the transmitter antenna driver's frequency because its parameters change along with changes in temperature and pressure down hole. Changing the attenuator tuning will inevitably reduce its stop-band losses and result in elevating the voltage at the input of receiver circuitry that might exceed a safe level.

Tracking the transmitter synch frequency and sequential real time re-tuning the attenuation device can require parametric reactive elements such, for instance, pre-saturated inductors. To use inductors a biasing field supplied by an external "exchangeable" magnet or additional winding carrying a direct current would be required. These, however, would result in unreasonable and often non-achievable stability requirements and introduce additional noise. On other hand, semiconductor voltage controlled capacitors, or varicaps, are impractical due to their low initial capacitance and small voltages that such a device can withstand. However, even if these design constraints were overcome, the attenuator tuning requirements would also deteriorate the NMR tool logging speed that is associated with the time required to accomplish tuning.

Thus, there is a need for a dedicated NMR antenna signal conditioning circuitry that overcomes the limitations discussed above.

SUMMARY OF THE INVENTION

The present invention provides an improved and novel active signal conditioning circuitry for NMR transmitter/receiver antenna that is free from the limitations of known NMR antenna designs. Thus, it is an object of the present invention to provide signal conditioning circuitry for connection between a combined NMR transmitter/receiver antenna and the associated receiver circuitry to avoid the problems associated with known NMR transmitter/receiver antennas discussed above. The NMR transmitter/receiver antenna circuitry provided by the present invention comprises electronic circuitry which enables receiver antenna circuit protection from high voltage applied during RF transmitter pulses, provides dumping for the entire antenna in successive stages and eliminates re-tuning during sweeping of the antenna frequency.

Further features and advantages of the invention will become more readily apparent from the following detailed description, when taken in conjunction with the accompanying drawings.

BRIEF OF THE DRAWINGS

DETAILED DESCRIPTION OF A PREFERRED EMBODIMENT

Figure 1:
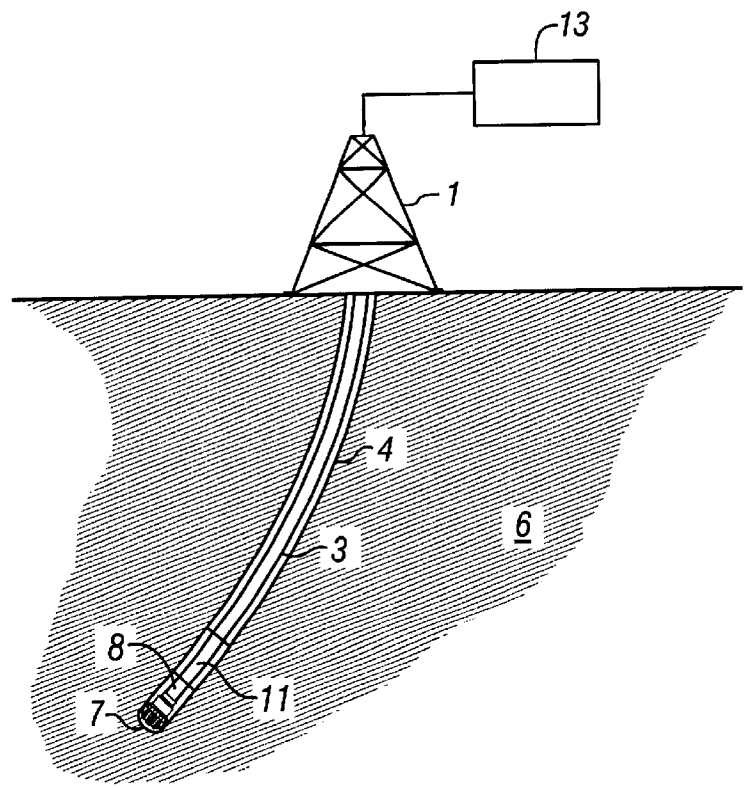
FIG. 1 is an illustration of a typical NMR tool deployed in a monitoring while drilling bore hole environment.

A drilling operation environment for deployment down hole of an NMR tool according to the present invention is shown deployed in a monitoring while drilling environment in FIG. 1. As shown in FIG. 1, a drill rig 1 drives a drill string 3 that, which typically is comprised of a number of interconnecting sections. A down hole assembly 11 is formed at the distal end of the drill string 3. The down hole assembly 11 includes a drill bit 7 that advances to form a bore 4 in the surrounding formation 6. A portion of the down hole assembly 11, incorporating an electronic system 8. The electrical system 8 may, for example, provide information to a data acquisition and analysis system 13 located at the surface. The electrical system 8 includes one or more nuclear magnetic resonance (NMR) tools. The NMR tool includes a NMR spectrometer, which is well known in the art. The electrical system comprising the NMR tool and spectrometer further comprise the active signal conditioning circuitry for the monitoring while drilling NMR antenna of the present invention.

Figure 2:
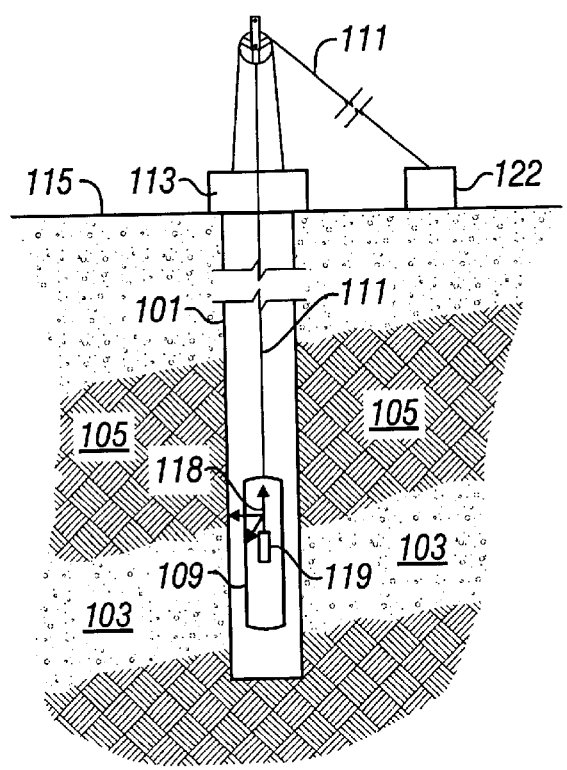
FIG. 2 is an illustration of a typical NMR tool deployed in a wire line logging borehole environment.

Turning now to FIG. 2 a wire line deployment of the present invention is depicted. FIG. 2 schematically shows a well bore 101 extending into a laminated earth formation, into which well bore a logging tool including NMR antenna and sensors and electronics as used according to the present invention has been lowered. The well bore in FIG. 2 extends into an earth formation which includes a hydrocarbon-bearing sand layer 103 located between an upper shale layer 105 and a higher conductivity than the hydrocarbon bearing sand layer 103. An NMR electronic logging tool 109 having NMR antennas and associated electronics has been lowered into the well bore 101 via a wire line 111 extending through a blowout preventor 113 (shown schematically) located at the earth surface 115. The surface equipment 122 includes an electric power supply to provide electric power to the antenna 118 and a signal processor to receive and process electric signals from electronics 119. Alternatively, a power supply and signal processor are located in the logging tool. In the case of the wire line deployment, the wire line may be utilized for provision of power and for data transmission.

The NMR tool 109 includes a NMR spectrometer, which is well known in the art. The electrical system comprising the NMR tool further comprises the active signal conditioning circuitry for the well logging NMR spectrometer of the present invention. FIGS. 1 and 2 are shown for purposes of providing an example of the deployment of a NMR tool utilizing the present invention in a wire line logging and monitoring while drilling environment, however, are not intended to limit the use of the present invention to a particular application.

Figure 3:
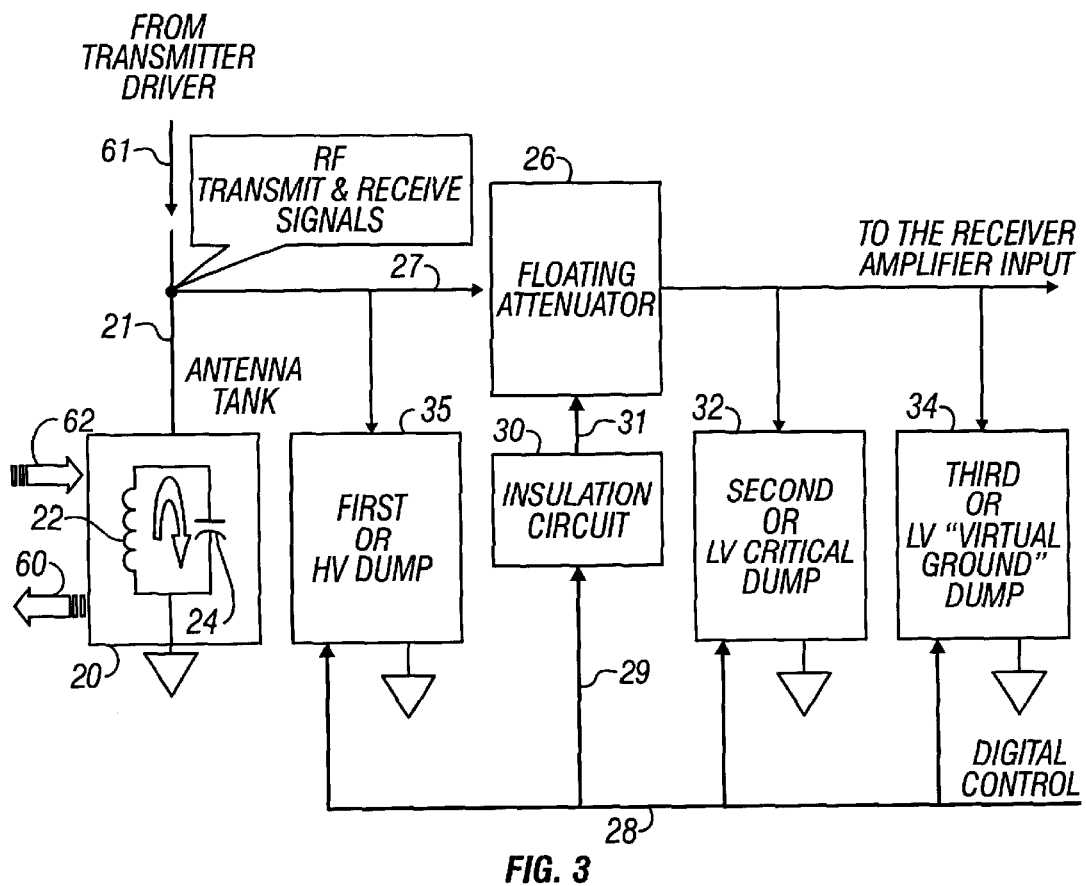
FIG. 3 is a schematic representation of a preferred embodiment of the present invention.

Turning now to FIG. 3, a schematic representation of a preferred embodiment is illustrated. In a preferred embodiment, during a high voltage RF excitation pulse 61, or transmission mode when the transmitter RF magnetic field 60 has been irradiated into the formation, an electrically floating attenuator 35 is provided between the antenna terminals and the receiver electronic circuitry. The attenuation level provided is sufficiently high to protect the receiver electronics from damage by excessive transmission pulse voltages 61. The preferred attenuation value is determined according to magnitude of this pulse voltage 61 and the specifications given for particular electronic receiver components. Preferably attenuation is provided such that signals present at the receiver circuitry input terminals do not exceed the power supply voltage for the receiver circuitry. The preferred attenuation device 35 also does not reduce the antenna quality value Q. The floating attenuator 35 is controlled by the NMR tool's on-board microprocessor (not shown) through digital control lines 28 and insulation circuit 30.

In a preferred embodiment, the circuitry provided by the present invention substantially dissipates all antenna power stored in the antenna circuit 20 as a result of generating the transmission pulse. This power should be removed from the circuits reasonably quickly to enable tool measurements with short time delays between transmission RF pulse and NMR formation response. In the preferable embodiment the dissipation process preferably comprises of two sequential transmitter-dumping stages.

Within the first transmitter-dumping stage the high voltage dump 26 having almost negligible intrinsic impedance to the electrical current flow dissipates the most significant portion of stored energy. This first stage reduces magnitude of the tank voltage down to conform to the safe level of receiver circuit for less than a microsecond since the operation of the dump 26 has been enabled.

After this initial first stage reduction, i.e., at the beginning of the second transmitter dumping stage, the floating attenuator 35 is disabled and ready to conduct electrical current through without attenuation.

Simultaneously with disabling the floating attenuator 35, the low control circuitry enables the voltage dump 32 and disables the high voltage dump 26 i.e., its conductance again becomes negligible. The low voltage dump 32 starts to conduct electrical current with a throughout impedance equal to or close to the critical impedance of the antenna tank 20.

During this second transmitter-dumping stage the remaining antenna energy is dissipated within the time of one to one and a half free tank 20 oscillations. Notice that during all these operations the low voltage or "virtual ground dump" 34 remains disabled and it does not conduct electrical current.

For those skilled in the art it should be understood that selecting two transmitter energy removal stages as previously described has been done only to avoid overheating and damaging components in the low voltage dump 32. Thus, if the high voltage dump 26 were constructed as critical, it would be difficult to maintain integrity and mechanical reliability of the resistors that are needed. Instead, during the first transmitter-dumping stage a rush current through the dump 26 is directed to the massive tool analog ground, usually a tool chassis, that can easily withstand such an impact.

Selecting the high voltage dump 26 to not be critical but rather reliable has been a justification for using the low voltage critical dump 32. Thus, it could be also seen that after non-critical high voltage dump 26 is disabled, there would remain low voltage free oscillations in the tank 20 that are due to a well known nature of transient processes in the resonant circuits. That is, the low voltage dump 32 has completed removal of these oscillations within their one to one and a half periods. After completion of the second transmitter-dumping stage the low voltage critical dump 32 is disabled and stops conducting electrical current; the attenuator 32 will remain in its conducting condition until the formation NMR response is fully acquired.

For those skilled in the art it also should be understood that two-stage transmitter dumping described the above should not be considered as a limitation to the overall transmitter dumping method. For example, switching from a two stage transmitter dumping circuit to an alternative embodiment wherein to a single stage critical dump is within the scope of the present invention, as soon as the industry is able to supply electronic parts capable of withstanding rush currents and overheating in harsh environments in which the logging tools are operating.

During the delay between the end of the second transmitter-dumping stage, i.e., final removal of the energy stored in the tank 20 after transmission 60, and arrival of the formation NMR response 62, the present invention continues dumping any parasitic oscillations in the antenna 20. This provides the SNR conditioning prior to arrival of the formation echo response 62 and is accomplished using non-critical antenna shunting by a "virtual ground" or "soft" dump 34. In particular, this dump prevents inducing free oscillations in the antenna 20 from any internally generated electrical noise that might couple back into the tank 20.

By itself, during the receiving mode, the preferred signal conditioning circuitry preferably does not affect the antenna Q and provides minimum possible attenuation of the induced signal on its way to the receiver input amplifier. In a preferred embodiment, preferably only a 10% or less reduction in the SNR occurs due to the use of preferred electrical components in dumps and attenuator having finite electrical and electromagnetic parameters. However, some SNR reduction still might happen due to possible resonant frequency shifts between transmission and receive modes. This would be a result of changes in imaginary component of the conditioning circuits'input impedance depending on the tool operating mode, finite attenuation value in the attenuator 35 while transmitting 60 associated with stray capacitance in and between active elements. An additional and insignificant SNR reduction could be also due some active losses occurring in the circuit while in the receiving mode.

The present invention provides active signal conditioning circuitry that enables high quality NMR spectrum measurements and does not require re-tuning while changing the spectrometer transmitter/receiver antenna frequency. The functional block diagram of a preferred embodiment of the present invention and its modules are illustrated in FIG. 3.

The antenna tank 20, or antenna module incorporates a primary inductive antenna 22, capacitor(s) 24 bank, leads 21 and 27, control lines 28 and 29 that are selectively coupled to the tank circuit. The high voltage (HV) dump active circuit 26, when activated through digital control line 28, dissipates the high RF voltage signal oscillating in the antenna tank 20 until the signal is reduced to a few tenths of a volt within a relatively short time, typically below one microsecond. The active elements of the HV dump circuit 26 are selected to withstand the full antenna transmitter voltage 61 in the open or inactive state. It also presents a sufficiently low throughput resistance capable of withstanding a pulse surge current in the conduction state when the tank 20 has been shunted by this resistance to quickly remove the energy stored during previous transmission pulse.

High voltage floating attenuator 35, as shown in FIG. 3, does not conduct electrical current while the spectrometer is in the transmission mode. In turn, in the receive mode, after the high voltage dump 26 operation is completed, the floating attenuator module 35 provides minimal attenuation, presenting a relatively low on-resistance. Due to the electrical position of the floating attenuator 35, in series with the hot antenna lead 27, the floating attenuator 35 and its control inputs 31 are galvanically separated from the analog ground and digital control lines 28. The attenuator 35 electrical components are capable of withstanding the primary transmission pulse voltage 61. The attenuator 35 is engaged and conducts current only if receives a respective signal through the respective digital control. In the preferred embodiment this signal is to be high state on the line 31. In the case of circuitry failure due to power loss, the control signal goes to substantially zero and thus prevents conduction of current through the floating attenuator and applying high transmitter voltage 61 to the receiver input avoiding damages. The ground insulation circuit 30 enables this analog ground-referenced digital control signals 31 to be applied to control the inputs of the floating attenuator 35.

The low voltage (LV) dump 32 is an active circuit that dissipates the remaining antenna power after the HV dump 26 is complete. The LV dump 32 is designed so that the internal impedance of the module in the conduction mode is equal to the antenna's characteristic or critical impedance. The LV dump 32 is also designed for low capacitive leakage from its input to output in the non-conductive state. The virtual ground dump 34 creates a virtual ground for the receivers input. In operation, after the critical dump 32 operation is over and prior to reception of pulse 62, the virtual ground dump 34 forms a virtual shunt from the antenna 20 through the floating attenuator 35 to analog ground. This is enabling suppression of any parasitic oscillations that may start in the antenna 20 due to the tool intrinsic noise.

Figure 4:
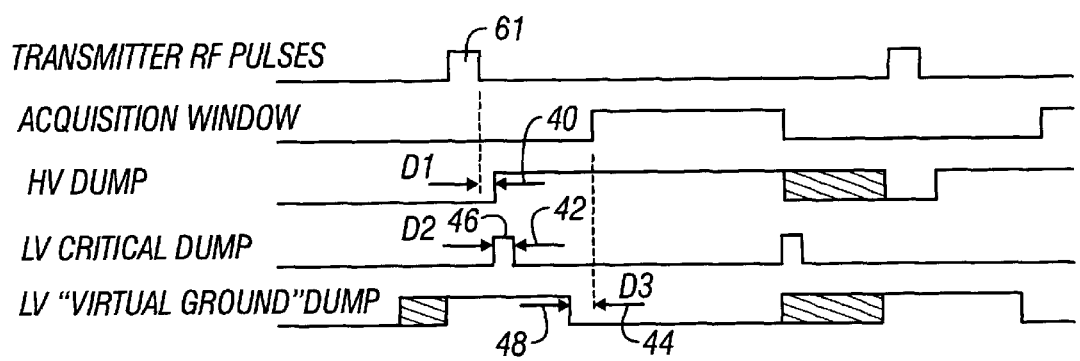
FIG. 4 is a timing diagram for a preferred embodiment of the present invention.

Turning now to FIG. 4, the sequence of operations of the present invention is illustrated with the reference to the front-end of transmitter voltage pulse 61. After the transmission is completed and with a delay equal to 2 to 3 periods of free RF oscillation in the antenna tank circuit, represented in FIG. 4 by period 40, the first HV dump 26 is switched on to dissipate the main portion of the transmitter energy. The active components in the dump circuit are capable of conducting very high surge current over a short period of time.

While the amount of energy stored in the antenna is relatively small, on the order of a few milliwatts, the surge current can reach 500 to 1000 amperes. The above-mentioned delay of 2 to 3 periods of free RF oscillation is provided to ensure that the transmitter electronic drivers themselves do not experience overloading due to the conduction of the first HV dump 26.

Approximately 10 microseconds after the end of the transmission pulse 61, the floating attenuator 35 and the critical dump 32 are switched on by digital control pulse 46 and the antenna tank 20 is connected to the analog ground by the critical dump impedance. Depending on the match between the antenna critical impedance and impedance of the dump 32 the critical dump impedance enables reduction of the antenna voltage down to a microvolt level within one and one-half antenna oscillation periods.

Once the critical dump ground reduces the voltage to the microvolt level, the virtual ground dump 48 process is started. For safety reasons, however, the virtual ground 48 process is started at 20 microseconds after the end of the transmission pulse 61. The threshold voltage, however, and respective time is determined by the type of active components being used in the virtual module. The virtual ground dump is preferably comprised of forward biased diodes, thus the signal should not exceed the biasing voltage minus the diode's threshold voltage.

The state of the critical dump 32 during the "virtual ground" dump is preferably disabled to avoid the possibility that switching active circuitry from conductive to nonconductive mode may also induce minor oscillations in the antenna. These oscillations may not be effectively rejected, thus, it is preferable that the critical dump is disabled for approximately 50 micro seconds 44 before the beginning of the reception mode 62.

The virtual ground dump 34 is considered to be "soft", based on the assumption that the control circuit that controls this module and the dump itself do not generate any sharp-edged wave fronts. This soft dump minimizes the amount of electrical charge that can be coupled back into the antenna, thereby minimizing parasitic oscillations that would be caused by these coupled charges.

All active components, which preferably are metal oxide semiconductor field effect transistors (MOSFETs) have a parasitic capacitance between their electrodes that is associated with both the physics of the design and their mechanical layout. Thus, in most cases the circuit compensates for the capacitance between the drain and the source of the MOSFETs, anode and cathodes of diodes, and other sources of capacitance. This capacitance varies significantly depending on the voltage applied between the electrodes. In general, parasitic capacitance is inversely proportional to the applied voltage. Thus, the components comprising the present invention preferably exhibit minimal capacitance. Selection of components with minimum capacitance substantially eliminates otherwise unavoidable parasitic current leakage through the floating attenuator 35 in the transmission mode, reduction of the overall resonant frequency of the antenna 20 going from transmission mode to receiver mode, and reduction of additional attenuation prior to pre-amplification of the signal. These combined effects can also reduce the spectrometer signal to noise ratio.

Figure 5:
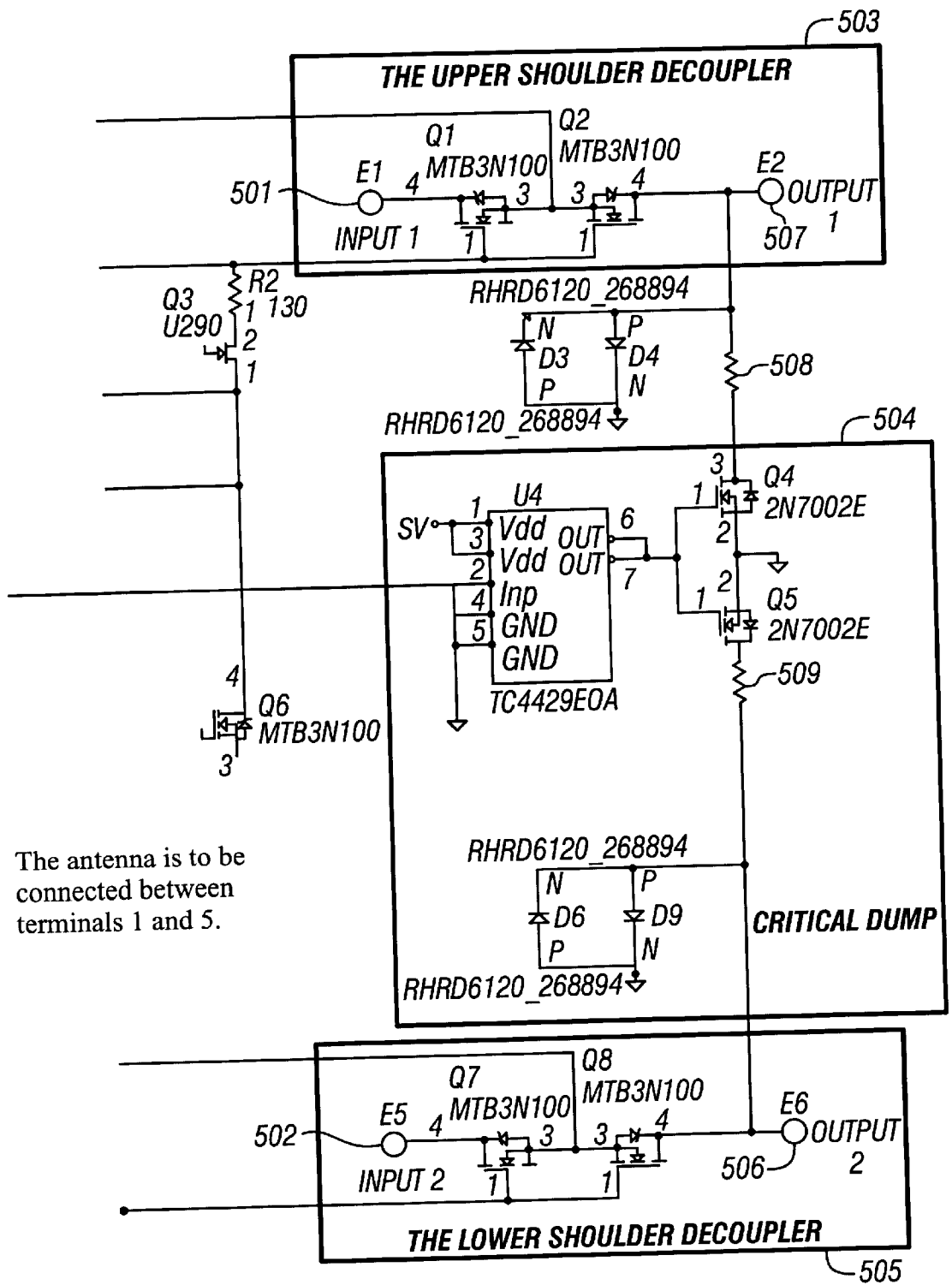
FIG. 5 is a schematic diagram showing an example of circuitry utilized in a preferred embodiment of the present invention.
Figure 6:
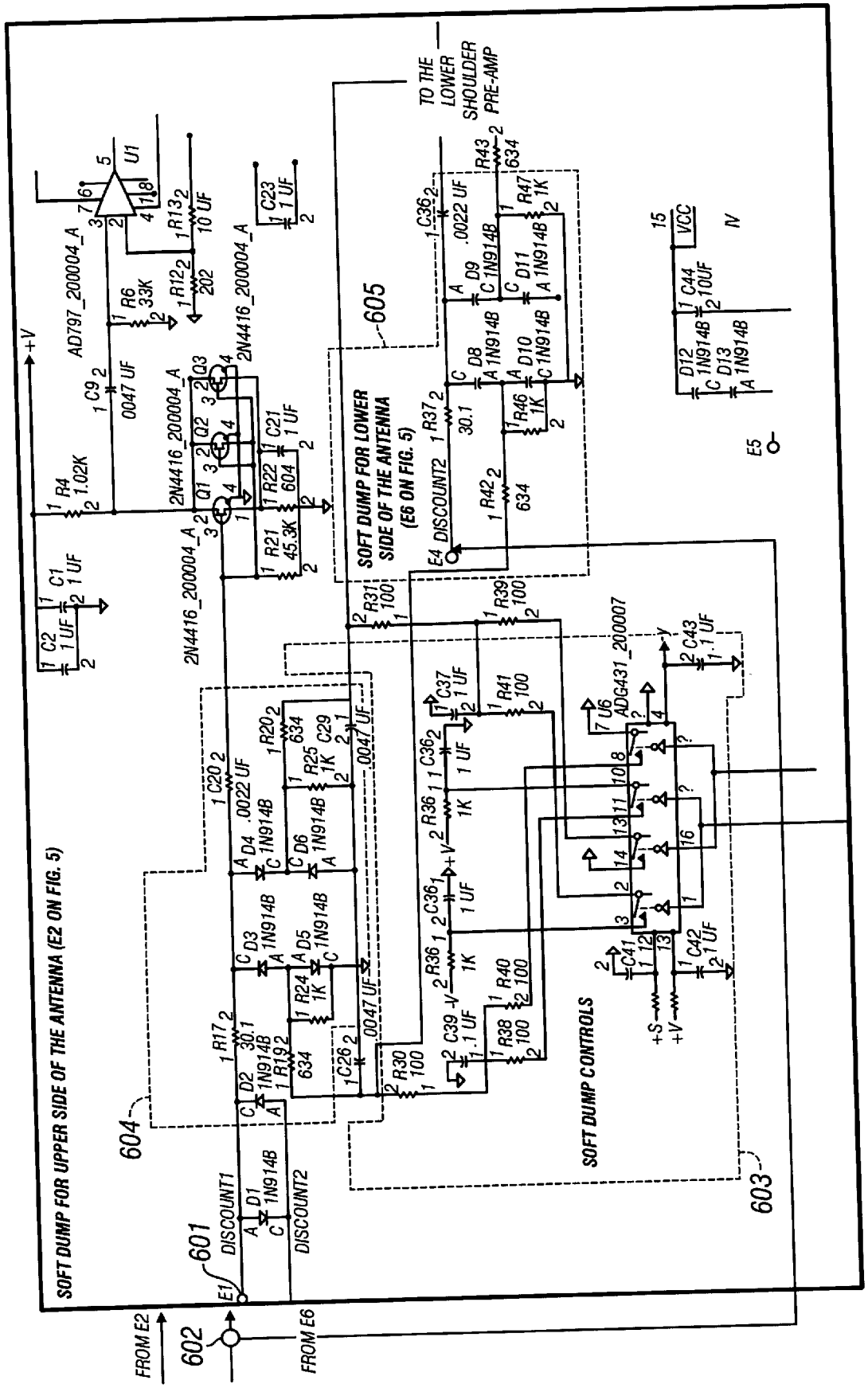
FIG. 6 is a schematic diagram showing an example of circuitry utilized in a preferred embodiment of the present invention.

Turning now to FIG. 5, a preferred embodiment of the critical dump and decoupling circuitry of the present invention is illustrated. The NMR antenna is connected between input terminals 501 and 502. FIG. 5 illustrates circuitry comprising upper shoulder attenuator 503. The output 507 of upper shoulder attenuator 503 is connected to critical dump 504 through resistor 508 with the value equal to the half of the antenna's critical impedance, as shown in FIG. 5, and to the input 601 of "virtual ground" dump 604, as shown in FIG. 6. The output 506 of lower shoulder attenuator 505 is connected to the critical dump 504 through resistor 509 with the value equal to the half of the antenna's critical impedance, as shown in FIG. 5, and to the input 602 of "virtual ground" dump 605, as shown in FIG. 6. As it could be seen from the FIG. 5, when the critical dumps of both upper and lower shoulders are enabled, i.e. they are conducting current, the total shunt value for the antenna 20 comprises of two resistors 508 and 509 connected in series. Their combined resistance will match the critical impedance of the antenna 20. A preferred embodiment of the circuitry comprising critical dump 504 is shown in FIG. 5.

Turning now to FIG. 6, a preferred embodiment of the circuitry comprising the "virtual ground" dump 604 for the upper side of the antenna and the "virtual ground" dump 605 for the lower side of the antenna. The output 507 of upper shoulder attenuator 503 is connected to critical dump 504, as shown in FIG. 5, and to the input 601 of "virtual ground" dump 604, as shown in FIG. 6. The output 506 of lower shoulder attenuator 505 is connected to critical dump 504, as shown in FIG. 5, and to the input 602 of "virtual ground" dump 605, as shown in FIG. 6.

The foregoing description is for purposes of example only and not intended to limit the scope of the present invention that is defined by the following claims:

What is claimed is:

1. A method for investigating properties of an earth formation with a nuclear magnetic resonance (NMR) apparatus traversed by a borehole, comprising the steps for:

traversing a borehole adjacent a formation with a nuclear magnetic resonance (NMR) probe having a transmitter circuit for transmitting a radio frequency excitation pulse from an antenna and a receiving circuit for receiving voltages induced by precession of nuclei in the formation; inducing a static magnetic field in the formation from a permanent magnet in the NMR probe;

activating a floating attenuator before transmission of the RF pulse; and transmitting a radio frequency pulse from the antenna in the NMR probe thereby inducing a time varying magnetic field in the formation, the pulse having a fixed duration.

2. The method of claim 1 further comprising the steps for:

waiting a time after the NMR pulse duration has ended; and activating a high voltage active dump circuit for primary removing energy stored in the transmitter circuit after transmission of the radio frequency pulse.

3. The method of claim 1 further comprising the steps for:

de-activating the floating attenuator after energy stored in the transmitter circuit is primarily removed and thereby electrically connecting the receiver circuit to the antenna after the end of the transmission pulse duration; and activating a low voltage active critical dump circuit for further dissipating energy remaining in the transmission circuit after activating the high voltage circuit.

4. The method of claim 1 further comprising the step for:

activating a virtual ground dump after the active low voltage critical dump to suppress parasitic oscillations in the antenna until arrival the formation NMR response; and deactivating a virtual ground dump before arrival the formation NMR response in the antenna.

5. A method for investigating properties of an earth formation with a nuclear magnetic resonance (NMR) apparatus traversed by a bore hole, comprising:

traversing a bore hole adjacent a formation with a nuclear magnetic resonance (NMR) probe having a transmitter circuit for transmitting a radio frequency excitation pulse from an antenna and a receiving circuit for receiving voltages induced by precession of nuclei in the formation;

inducing a static magnetic field in the formation from a permanent magnet in the NMR probe;

activating a floating attenuator before transmission of the RF pulse;

transmitting a radio frequency pulse from the antenna in the NMR probe thereby inducing a time varying magnetic field in the formation, the pulse having a fixed duration;

waiting a time after the NMR pulse duration has ended;

activating a high voltage active dump circuit for primary removing energy stored in the transmitter circuit after transmission of the radio frequency pulse;

de-activating the floating attenuator after energy stored in the transmitter circuit is primarily removed and thereby electrically connecting the receiver circuit to the antenna after the end of the transmission pulse duration;

activating a low voltage active critical dump circuit for further dissipating energy remaining in the transmission circuit after activating the high voltage circuit;

activating a virtual ground dump after the active low voltage critical dump to suppress parasitic oscillations in the antenna until arrival the formation NMR response; and de-activating a virtual ground dump before arrival the formation NMR response in the antenna.

6. An apparatus for investigating properties of an earth formation with a nuclear magnetic resonance (NMR) apparatus traversed by a borehole, comprising:

a tool for traversing a borehole adjacent a formation comprising a nuclear magnetic resonance (NMR) probe having a transmitter circuit for transmitting a radio frequency excitation pulse from an antenna and a receiving circuit for receiving voltages induced by precession of nuclei in the formation;

a permanent magnet in the NMR probe for inducing a static magnetic field induced in the formation;

a floating attenuator for activation before transmission of the RF pulse;

an RF antenna for transmitting a radio frequency pulse from the antenna in the NMR probe thereby inducing a time varying magnetic field in the formation, the pulse having a fixed duration.

7. The apparatus of claim 6 further comprising:

a high voltage active dump circuit for primary removing energy stored in the transmitter circuit after transmission of the radio frequency pulse, activated after waiting a time after the NMR pulse duration has ended.

8. The apparatus of claim 6 further comprising:

a control circuit for deactivating the floating attenuator after energy stored in the transmitter circuit is primarily removed and thereby electrically connecting the receiver circuit to the antenna after the end of the transmission pulse duration; and a control circuit for activating a low voltage active critical dump circuit for further dissipating energy remaining in the transmission circuit after activating the high voltage circuit.

9. The apparatus of claim 6 further comprising the step for:

a virtual ground dump for activation after the active low voltage critical dump to suppress parasitic oscillations in the antenna until arrival the formation NMR response; and a virtual ground dump deacitivated before arrival the formation NMR response in the antenna.

10. An apparatus for investigating properties of an earth formation with a nuclear magnetic resonance (NMR) apparatus traversed by a borehole, comprising:

a tool for traversing a borehole adjacent a formation comprising a nuclear magnetic resonance (NMR) probe having a transmitter circuit for transmitting a radio frequency excitation pulse from an antenna and a receiving circuit for receiving voltages induced by precession of nuclei in the formation;

a permanent magnet in the NMR probe for inducing a static magnetic field induced in the formation;

a floating attenuator for activation before transmission of the RF pulse;

an RF antenna for transmitting a radio frequency pulse from the antenna in the NMR probe thereby inducing a time varying magnetic field in the formation, the pulse having a fixed duration;

a high voltage active dump circuit for primary removing energy stored in the transmitter circuit after transmission of the radio frequency pulse, activated after waiting a time after the NMR pulse duration has ended;

a control circuit for deactivating the floating attenuator after energy stored in the transmitter circuit is primarily removed and thereby electrically connecting the receiver circuit to the antenna after the end of the transmission pulse duration; and a control circuit for activating a low voltage active critical dump circuit for further dissipating energy remaining in the transmission circuit after activating the high voltage circuit;

a virtual ground dump for activation after the active low voltage critical dump to suppress parasitic oscillations in the antenna until arrival the formation NMR response; and a virtual ground dump deacitivated before arrival the formation NMR response in the antenna.

* * * * *